United States Patent
Feigenwinter et al.

(10) Patent No.: US 8,911,364 B2
(45) Date of Patent: Dec. 16, 2014

(54) SPINE RETRACTOR AND DISTRACTOR DEVICE

(75) Inventors: Gregor Feigenwinter, Lampenberg (CH); Beat Lechmann, Grenchen (CH); Roger Buerki, Chur (CH); Paul W. Pavlov, Nijmegen (NL)

(73) Assignee: DePuy Synthes Products, LLC, Raynham, MA (US)

( * ) Notice: Subject to any disclaimer, the term of this patent is extended or adjusted under 35 U.S.C. 154(b) by 1509 days.

(21) Appl. No.: 12/066,226

(22) PCT Filed: Sep. 8, 2006

(86) PCT No.: PCT/IB2006/004145
§ 371 (c)(1),
(2), (4) Date: Jun. 25, 2008

(87) PCT Pub. No.: WO2007/085909
PCT Pub. Date: Aug. 2, 2007

(65) Prior Publication Data
US 2008/0300465 A1    Dec. 4, 2008

Related U.S. Application Data

(60) Provisional application No. 60/715,189, filed on Sep. 8, 2005.

(51) Int. Cl.
*A61B 1/32* (2006.01)
*A61B 17/02* (2006.01)
*A61B 17/88* (2006.01)

(52) U.S. Cl.
CPC ..... *A61B 17/0293* (2013.01); *A61B 2017/0256* (2013.01); *A61B 17/8866* (2013.01)
USPC ........... 600/201; 600/219; 600/223; 600/231; 600/232; 600/233

(58) Field of Classification Search
CPC .................. A61B 17/0293; A61B 2017/0256; A61B 17/8866
USPC ............ 606/57; 600/201, 208, 215, 216, 219, 600/227, 231, 232, 233
See application file for complete search history.

(56) References Cited

U.S. PATENT DOCUMENTS

| 7,232,411 B2 * | 6/2007 | Dinkler et al. ................. 600/233 |
| 2002/0013514 A1 * | 1/2002 | Brau ............................. 600/213 |

(Continued)

FOREIGN PATENT DOCUMENTS

| WO | WO 2004/047650 A2 | 6/2004 |
| WO | WO 2007/085909 | 8/2007 |

OTHER PUBLICATIONS

International Search Report, dated Dec. 5, 2007, issued in International Application No. PCT/IB2006/004145.

(Continued)

*Primary Examiner* — Nicholas Woodall
*Assistant Examiner* — Christine Nelson
(74) *Attorney, Agent, or Firm* — Baker & Hostetler LLP

(57) ABSTRACT

A spine retractor and distractor device comprises spinal process clamps and a retractor assembly, which may be rotatably coupled with the spinal process clamps. The retractor assembly may include a retractor ring, or frame, and a plurality of retractor blades adjustably coupled to the frame, e.g., by clamps. The spinal process clamps can maintain a grip on the spinal processes of the patient, and distraction pliers may be used to impart a distraction force on the spinal process clamps to distract the spinal segments. Additionally, other components, features, or tools, e.g., a light source and/or a camera, can be mounted on the instrument.

18 Claims, 12 Drawing Sheets

(56) References Cited

U.S. PATENT DOCUMENTS

| | | |
|---|---|---|
| 2002/0165550 A1* | 11/2002 | Frey et al. .................. 606/85 |
| 2004/0002629 A1* | 1/2004 | Branch et al. .............. 600/210 |
| 2004/0230191 A1* | 11/2004 | Frey et al. .................. 606/57 |
| 2005/0075644 A1 | 4/2005 | DiPoto et al. |
| 2005/0277812 A1* | 12/2005 | Myles .......................... 600/231 |

OTHER PUBLICATIONS

U.S. Appl. No. 60/715,189, filed Sep. 8, 2005, Feigenwinter et al.

* cited by examiner

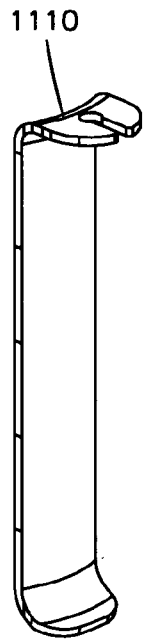 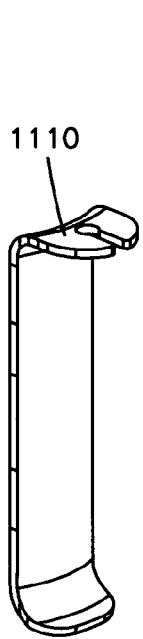 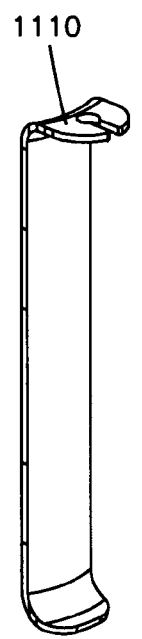 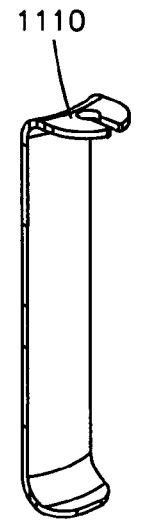
FIG. 10A    FIG. 10B    FIG. 10C    FIG. 10D
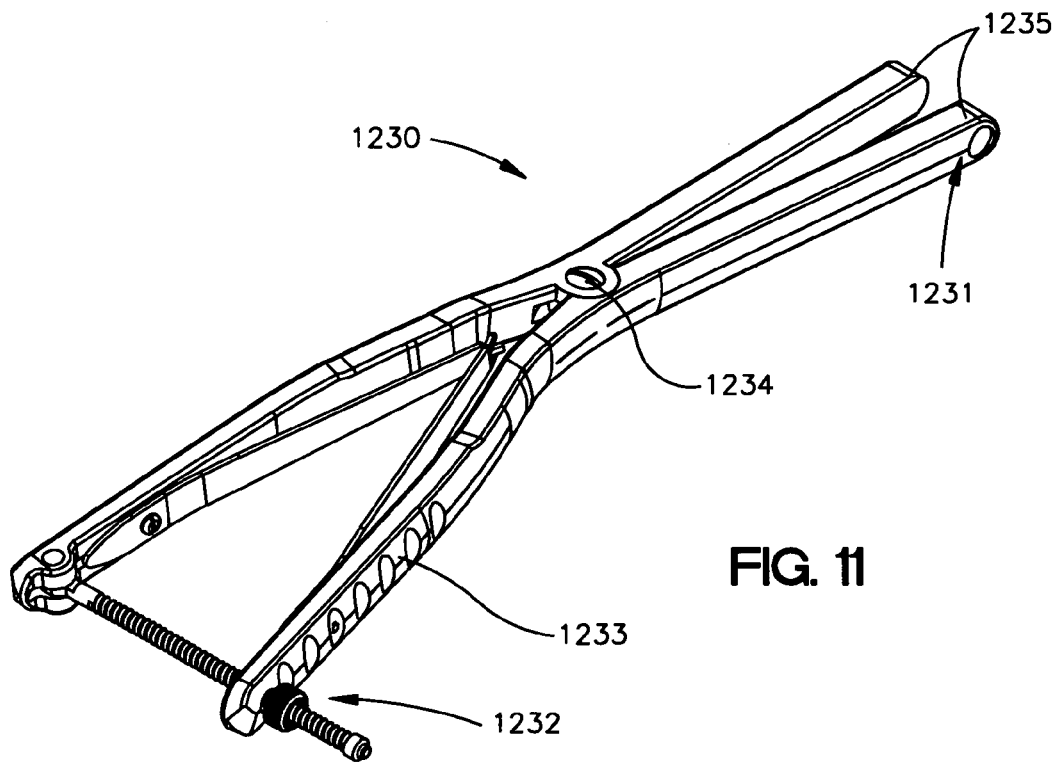
FIG. 11

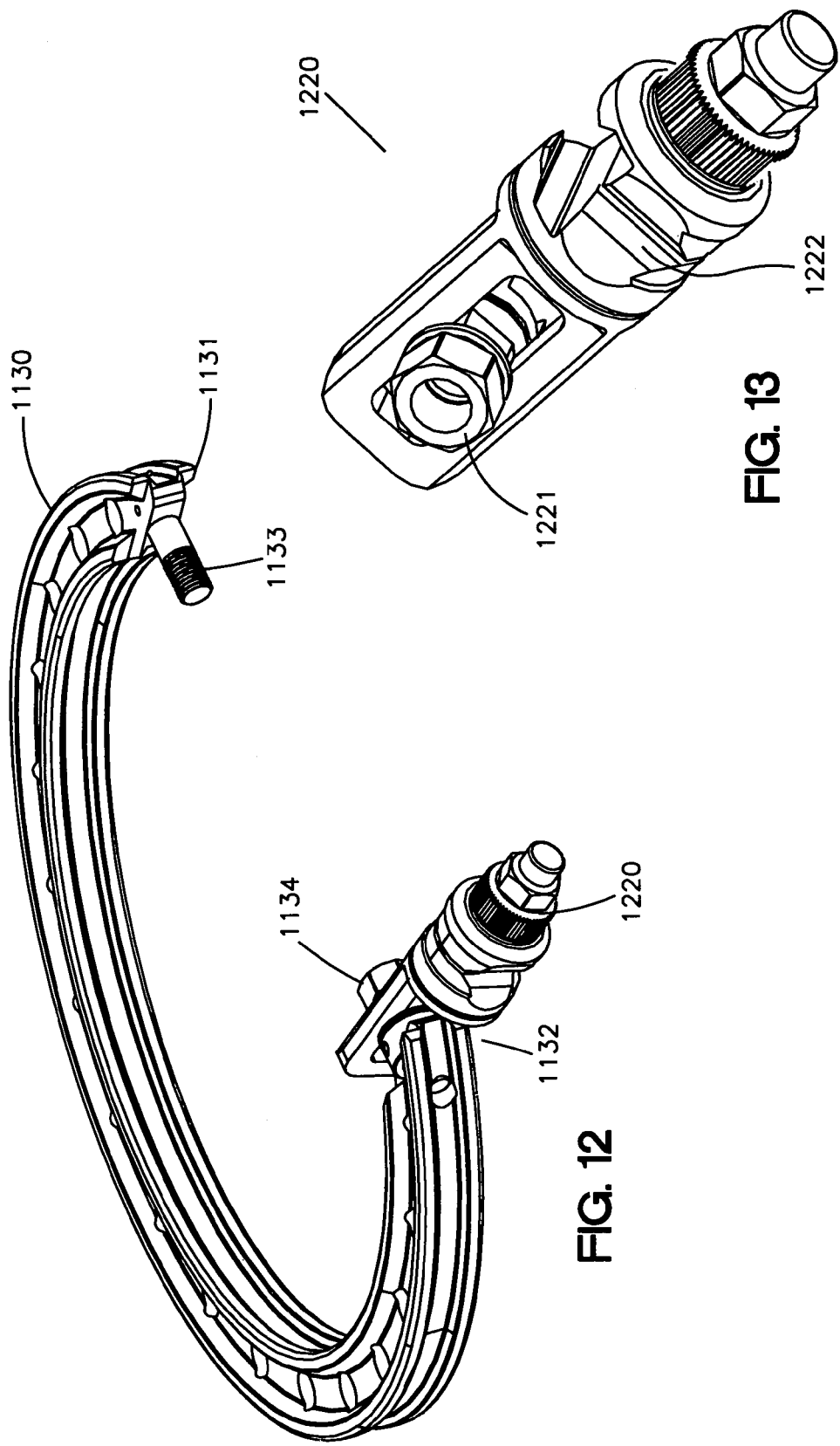

SPINE RETRACTOR AND DISTRACTOR DEVICE

CROSS-REFERENCE TO RELATED APPLICATIONS

This application is a national stage application under 35 U.S.C. 371 based on and claiming the benefit of International Application Serial No. PCT/IB2006/004145 filed on Sep. 8, 2006 and the benefit of priority from U.S. Provisional Application No. 60/715,189 filed on Sep. 8, 2005, the entire contents of each of which is incorporated herein by reference.

FIELD OF THE INVENTION

The invention relates to surgical devices and methods, and more particularly to devices and methods for surgical treatment of spinal injuries or disorders.

BACKGROUND OF THE INVENTION

Degenerated intervertebral discs are currently treated with fusion cages for arthrodesis, and lower grade degenerated discs are replaced by arthroplasty devices, i.e. total disc replacement (TDR) implants.

Standard surgical procedures for disc replacement with fusion or non fusion devices generally include the following steps, each of which are described in more detail below:
1. Create an approach to the selected disc;
2. Complete or partial removal of the selected disc or disc material (annulus and/or nucleus), e.g., discectomy; and
3. Insert the total disc replacement devices, or intervertebral spacers, or fixation devices such as screws, plates, rod systems, etc.

An approach through the soft tissue (i.e. skin, muscles, faciae) to a selected intervertebral disc(s) is created such that the soft tissue preferably is kept away from the site and the working area, e.g., by retractors or cannula. The purpose of the approach is to provide a suitable surgical approach and exposure to the appropriate degenerative disc level.

After a suitable approach is achieved the surgeon removes the affected disc material, such as for example the annulus, nucleus or both or portions thereof, with, e.g., curettes, or rongeurs or other instruments. The purpose of this step is to provide adequate discectomy and intervertebral endplate preparation.

After discectomy and endplate preparation, the endplates or vertebrae may be distracted to augment the intersection between the endplates and to create sufficient space for the replacement device. One way to perform this step is to use a distraction instrument.

Next, the surgeon inserts the replacement device in the appropriate position. Proper implant placement is beneficial to ensure optimal results, including segmental motion preservation. After the implant is inserted, the distraction instrument may be removed.

The intervertebral space between vertebral bodies may be approached with different techniques. Several techniques have been described in literature, such as anterior transperitoneal, trans-psoas (true lateral) or posterior approach through median incision. Another technique involves an extraforaminal approach for the insertion of spinal disc implants.

In order to accomplish a less invasive insertion of a TDR implant, suitable methods and instruments are needed to provide the respective support to the surgeon, including a distraction instrument and a mechanically stabilized retraction instrument. Two commonly accepted procedures for stabilization are:
1. use of the table in the operating room (OR) as reference; and
2. "binding" the instrument to the patient.

Considering the nerve root which must be controlled during the surgeon's manipulation, the mechanical link between the instrument and the table might have some short comings such as:
  the reference could be lost if the patient is moved on the table, whereas the nerve root is "bound" to the table; and
  the surgeon must manipulate outside the conventional sterile area, i.e. underneath the sterile covers on the OR table, which might contaminate the sterile incision area.

Discussion or citation of a reference herein will not be construed as an admission that such reference is prior art to the present invention.

SUMMARY OF THE INVENTION

There thus remains a need in the art to provide an apparatus and method for performing spinal procedures where retraction of soft tissue and distraction of spinal segments are mechanically linked to each other. The present invention realizes this need. The apparatus and methods of the present invention provide for retraction of soft tissue and distraction of spinal segments using the same device. A spine retractor and distractor device comprises spinal process clamps and a retractor assembly, which may be rotatably coupled with the spinal process clamps. The retractor assembly may include a retractor ring, or frame, and a plurality of retractor blades adjustably coupled to the frame, e.g., by clamps. The retractor assembly may have a fixed position with respect to the patient, and function to retract soft tissue to provide access to a desired portion of the spine. The spinal process clamps can maintain a grip on the spinal processes of the patient, and associated distraction pliers may be used to impart a distraction force on the spinal process clamps to distract the spinal segments. Additionally, other components, features, or tools, e.g., a light source and/or a camera, can be mounted on the instrument.

A method for performing spinal retraction and distraction may comprise the steps of securing two or more spinal process clamps to two or more spinal processes of a patient, retracting soft tissue around the spinal processes to expose a spine segment, and distracting the spinal segment using a distraction tool engaged with the one or more spinal process clamps. The retracting step may include engaging the soft tissue with one or more retractor blades adjustably coupled to a retractor ring which is coupled to the one or more spinal process clamps.

BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 10 is a perspective view illustration of various retractor blades according to an embodiment of the present invention;

FIG. 11 is a perspective view illustration of distraction pliers according to an embodiment of the present invention;

FIG. 12 is a perspective view of the retractor ring; and

FIG. 13 is a perspective view of a translation clamp.

DETAILED DESCRIPTION

Figure 1:
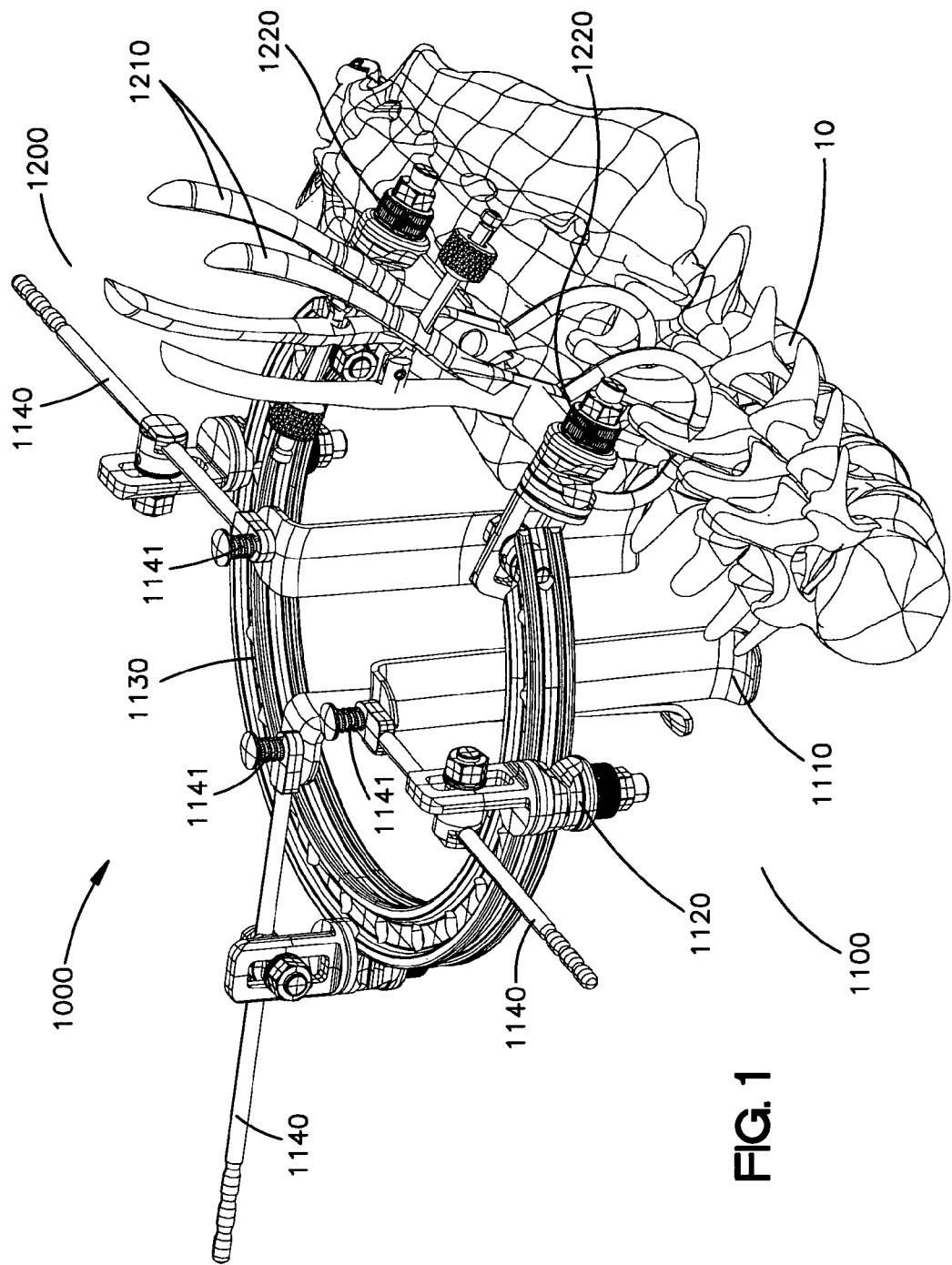
FIG. 1 is a perspective view illustration of a spine retractor and distractor device according to an embodiment of the present invention.

The systems and methods of the present invention provide for spinal retraction and distraction, for example, during surgical procedures on a spine. An exemplary spine retractor and distractor device 1000 is shown in FIG. 1. The spine retractor and device 1000 may include a retractor assembly 1100 and a distractor assembly 1200.

Figure 2B:
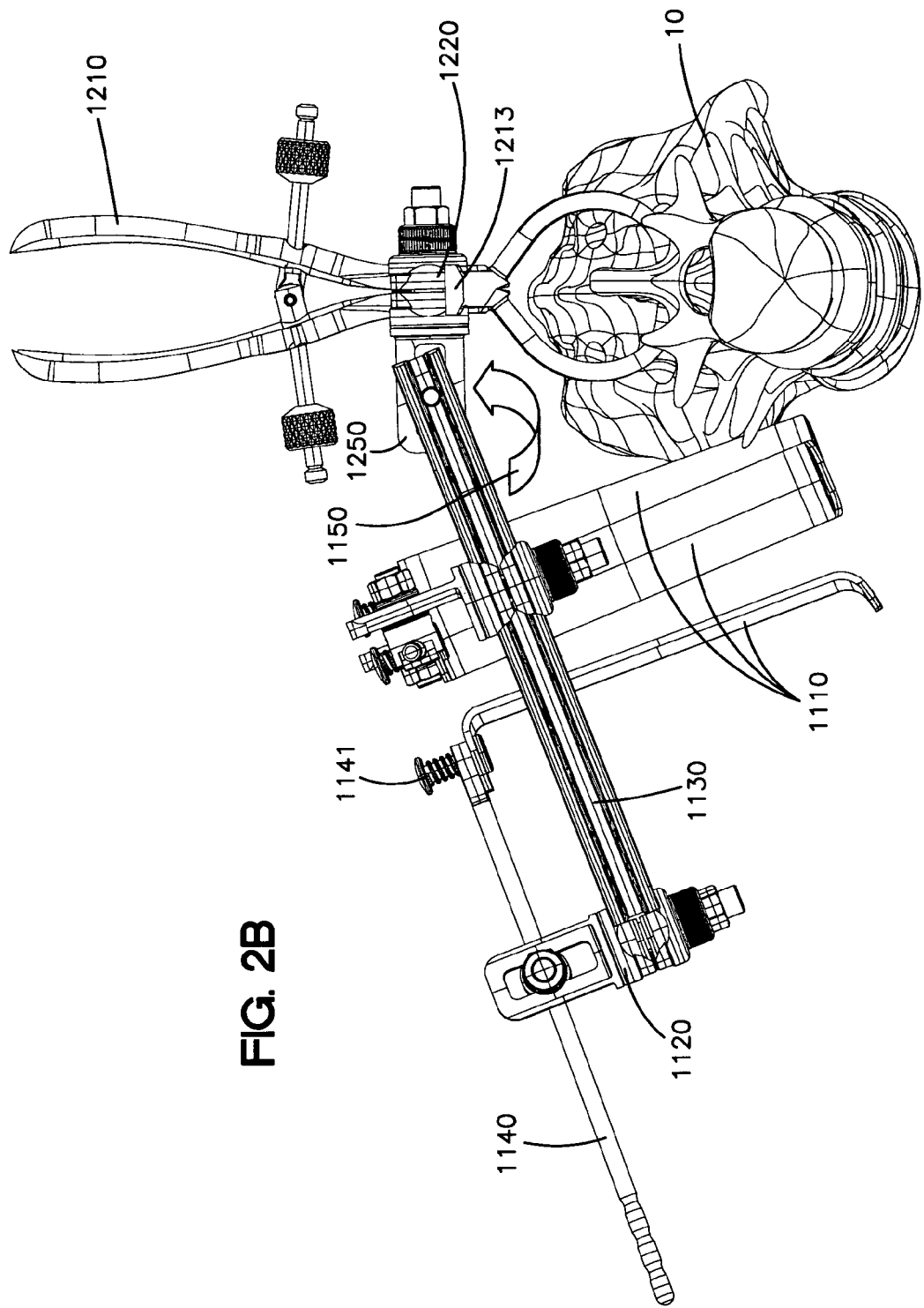
Figure 3:
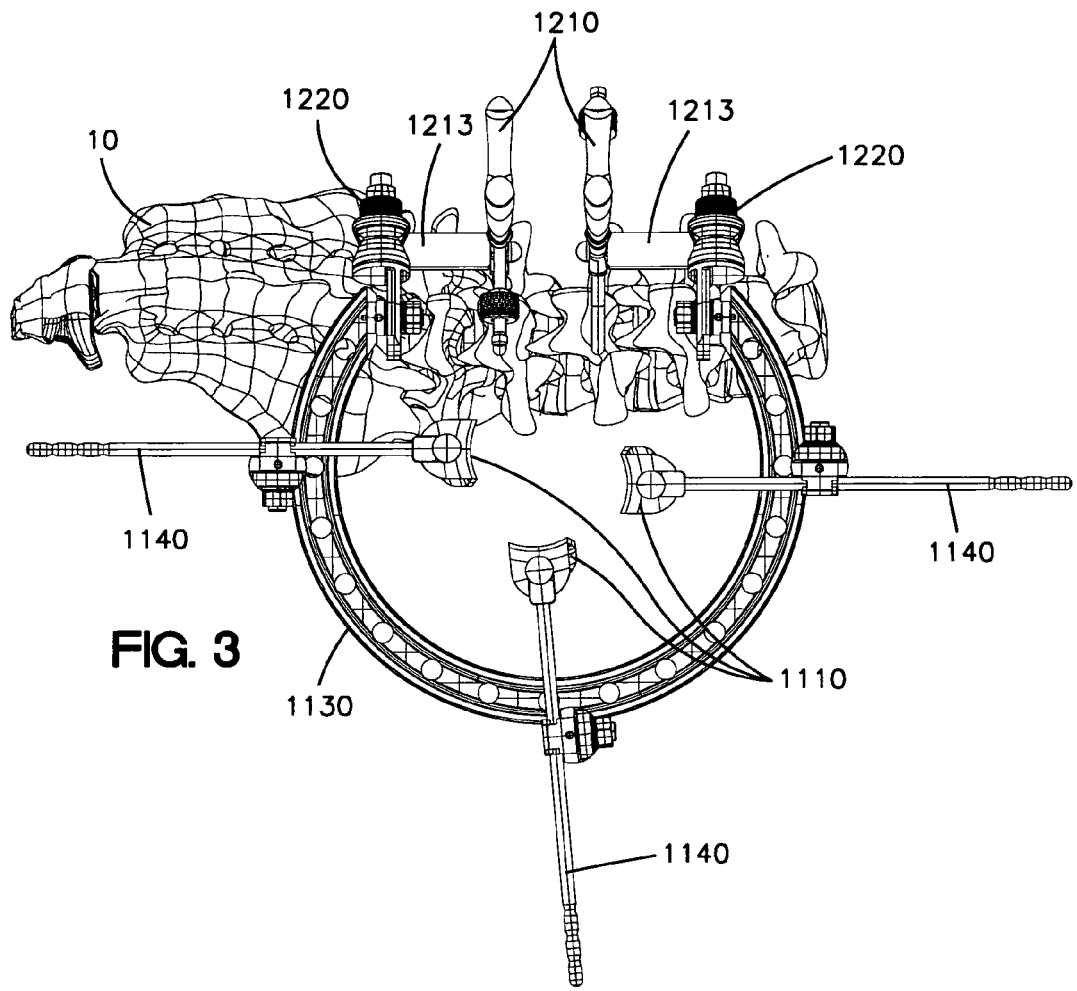
FIG. 3 is a top view illustration of a spine retractor and distractor device.

The retractor assembly 1100 is designed to hold soft tissue back from the approach and keep the incision open (see FIG. 3). The retractor assembly 1100 may preferably comprise a plurality of retractor blades 1110 adjustably coupled, e.g., by fixation clamps 1120, to a retractor ring 1130 that can be coupled to the distractor assembly 1200. The retractor ring 1130 may have a variable angle relative to the distraction clamps as shown by arrow 1150 in FIG. 2B, showing the angular adjustment of the retractor ring 1130 relative to the spinal processes clamps 1210.

Figure 7:
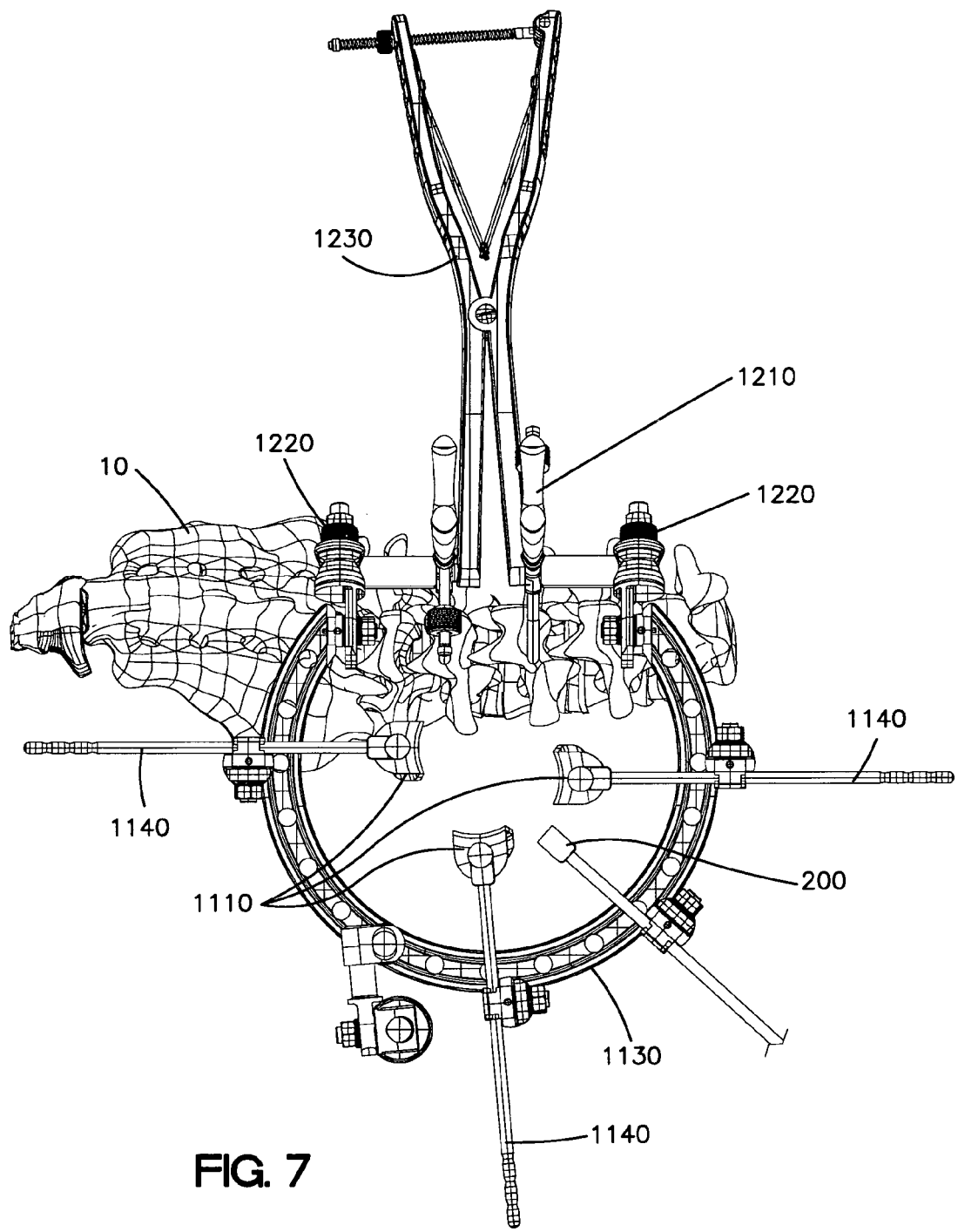
FIG. 7 is a top view illustration of a spine retractor and distractor device, showing distraction pliers engaged with spinal processes clamps.
Figure 8:
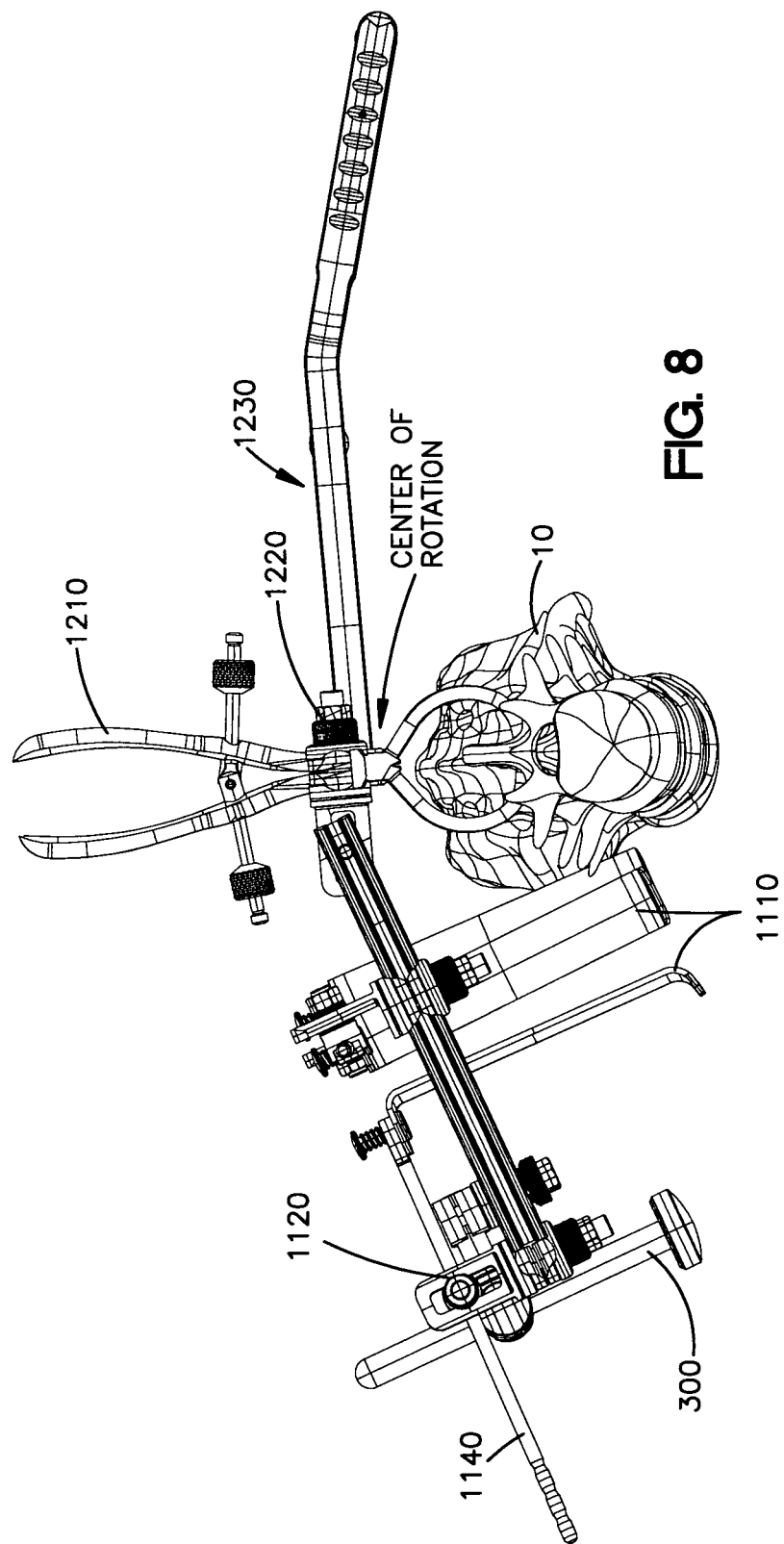
FIG. 8 is an end view illustration of a spine retractor and distractor device.
Figure 9:
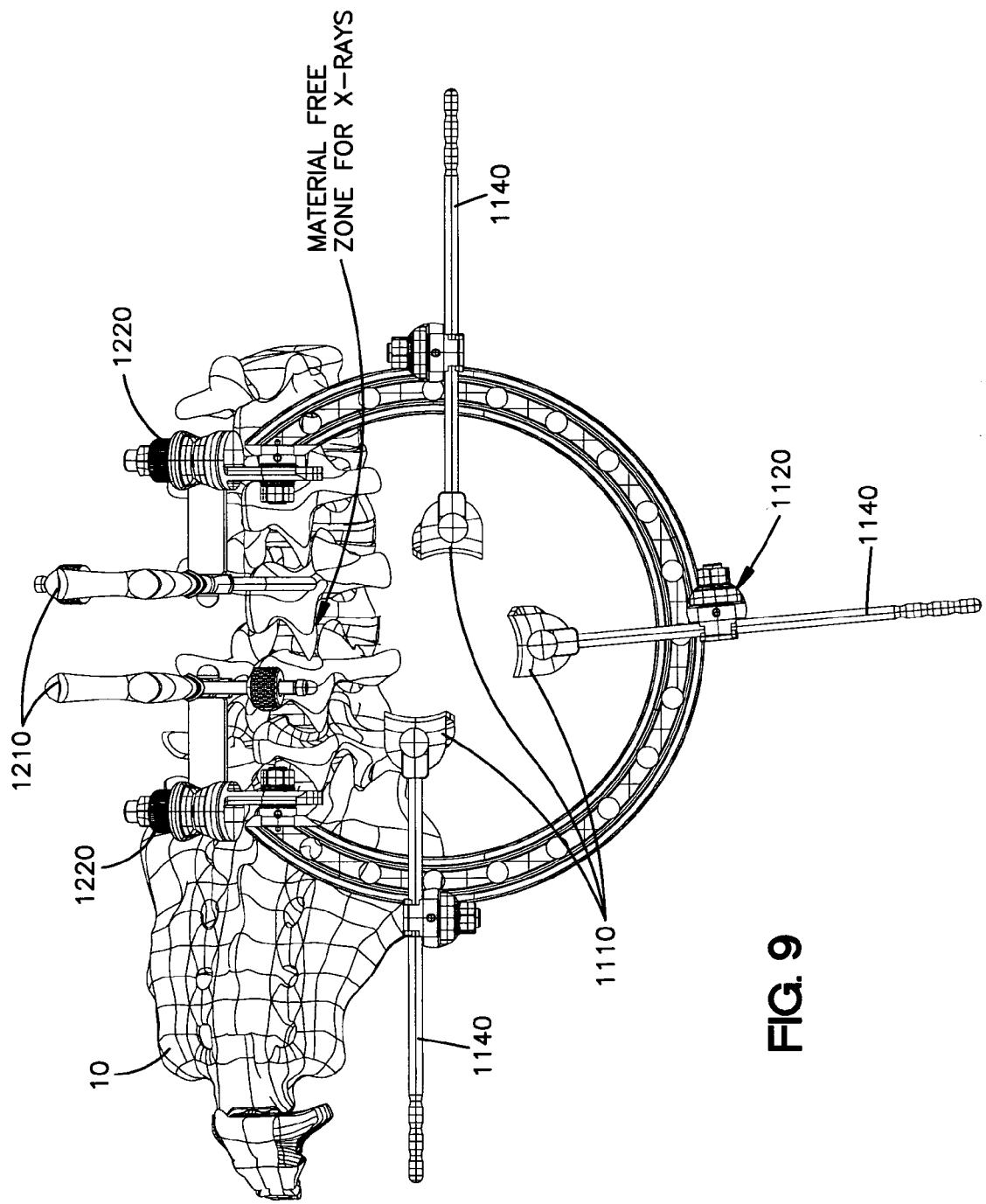
FIG. 9 is a top view illustration of a spine retractor and distractor device.

The retractor ring 1130, preferably having a circular shape, although any shape such as oval, square, rectangular, etc. is possible, transfers distraction forces between two spinal processes clamps 1210, and provides a structure to mount different clamps for different components, e.g., retractor blades 1110, light source 200, support arm 300, etc. The retractor ring 1130 is not a complete enclosed ring, rather it may have two ends which allow spinal processes clamps 1210 to be attached. The retractor ring 1130 with a variable angle, as shown in FIGS. 7-9, may have a cross section that allows the assembly of different clamps, such as spinal processes clamps 1210 (discussed later). The angle of the spinal processes clamps 1210 with respect to the retractor ring 1130 may be adjusted (discussed later). The retractor ring 1130 may or may not include an adjustable angle feature. Preferably a support arm 300 which attaches to the retractor ring 1130 ensures a reference marker for the patient. The retractor ring 1130 may preferably be made of a light and stable material, e.g. aluminum, stainless steel, PEEK (polyetheretherketone), or carbon fiber composite.

Figure 2A:
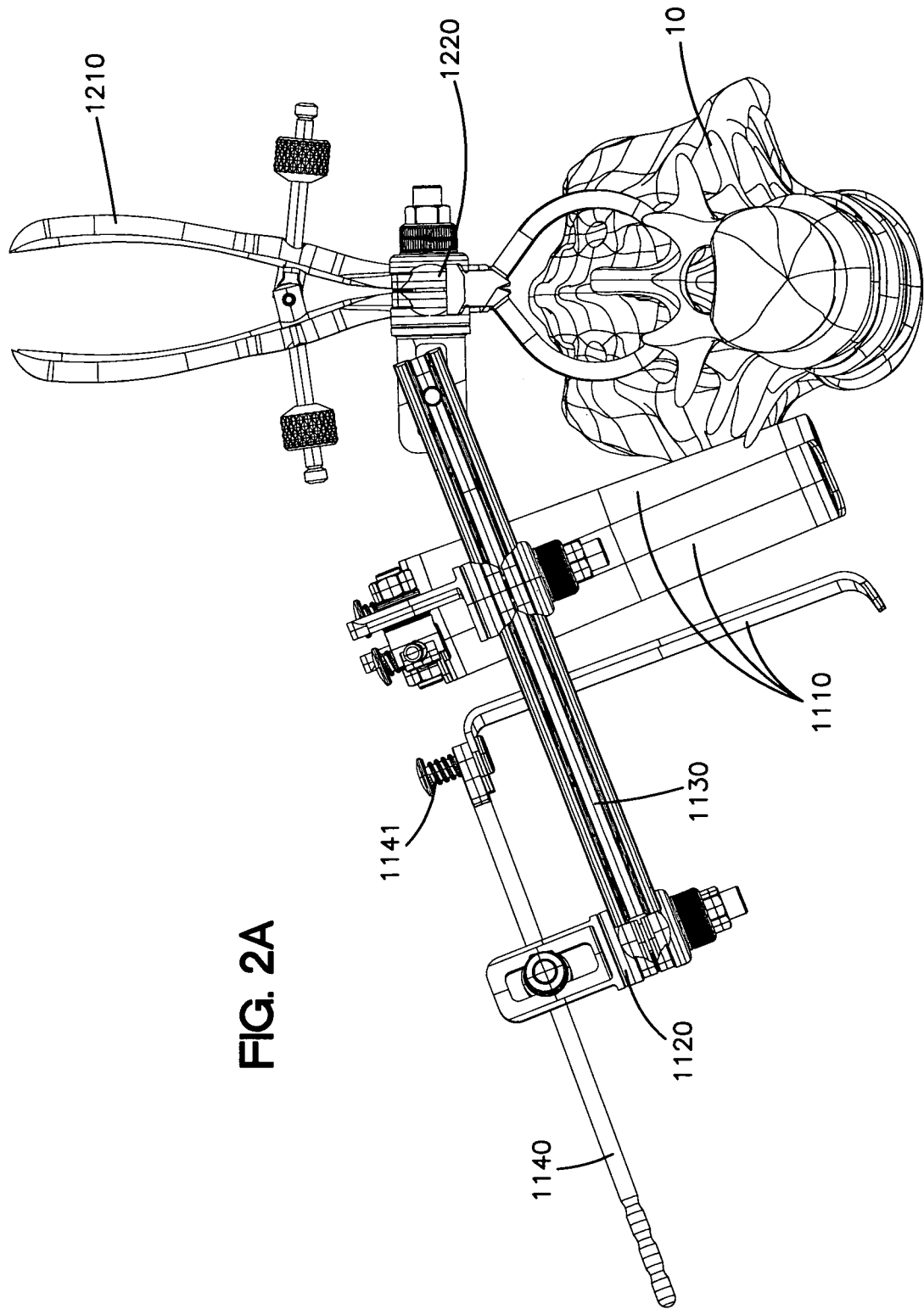
FIGS. 2A and 2B are end view illustrations of a spine retractor and distractor device.

The fixation clamps 1120, as shown in FIG. 2A, are connected to the retractor blades 1110 via a rod 1140 and screw 1141, allowing different degrees of freedom for the retractor blades 1110. The fixation clamps 1120 may also be utilized to hold additional components, such as for example light source 200 (see FIG. 7) and/or a camera (not shown). A support arm 300 for holding the position reference to the patient is shown in FIG. 8.

The retraction blades 1110 (as shown in FIG. 3) may be mounted as appropriate for the surgical procedure and the patient's anatomy. The retractor blades 1110 (as shown in FIG. 2A) may preferably have different lengths and strengths to provide a choice to the surgeon. Depending on the application, the surgeon is able to select the most appropriate retractor blades 1110 for the situation. Individual anatomy features of the patient requires different degrees of freedom to allow the retractor blades 1110 to function properly. As discussed, retractor blades 1110 may be mounted on various positions on the retractor ring 1130 to provide different degrees of freedom. The retractor blades 1110 hold the soft tissue back and keep the approach to the spinal column relatively clear. Further, the retractor blades may be bendable in order to adapt to soft tissue structures.

Figure 4:
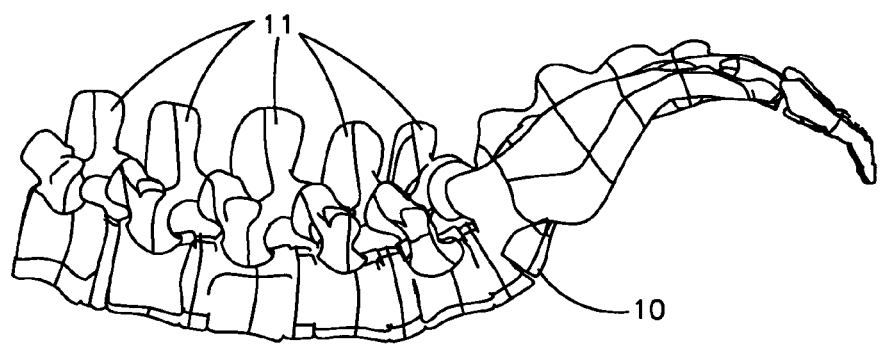
FIG. 4 is a side view illustration of a portion of a spine, showing spinal processes.
Figure 5A:
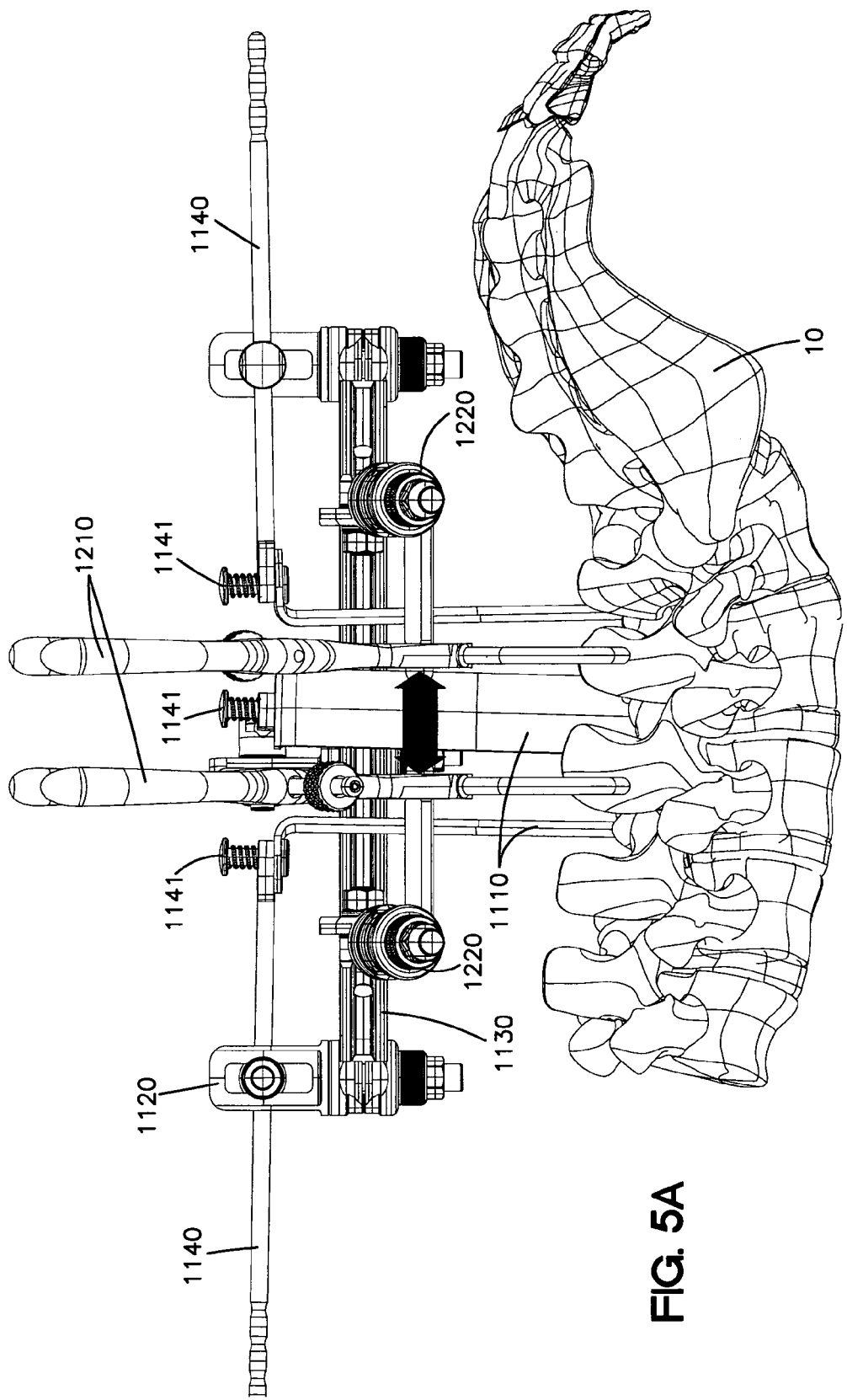
FIGS. 5A and 5B are side view illustrations of a spine retractor and distractor device before and during distraction of a spine.
Figure 5B:
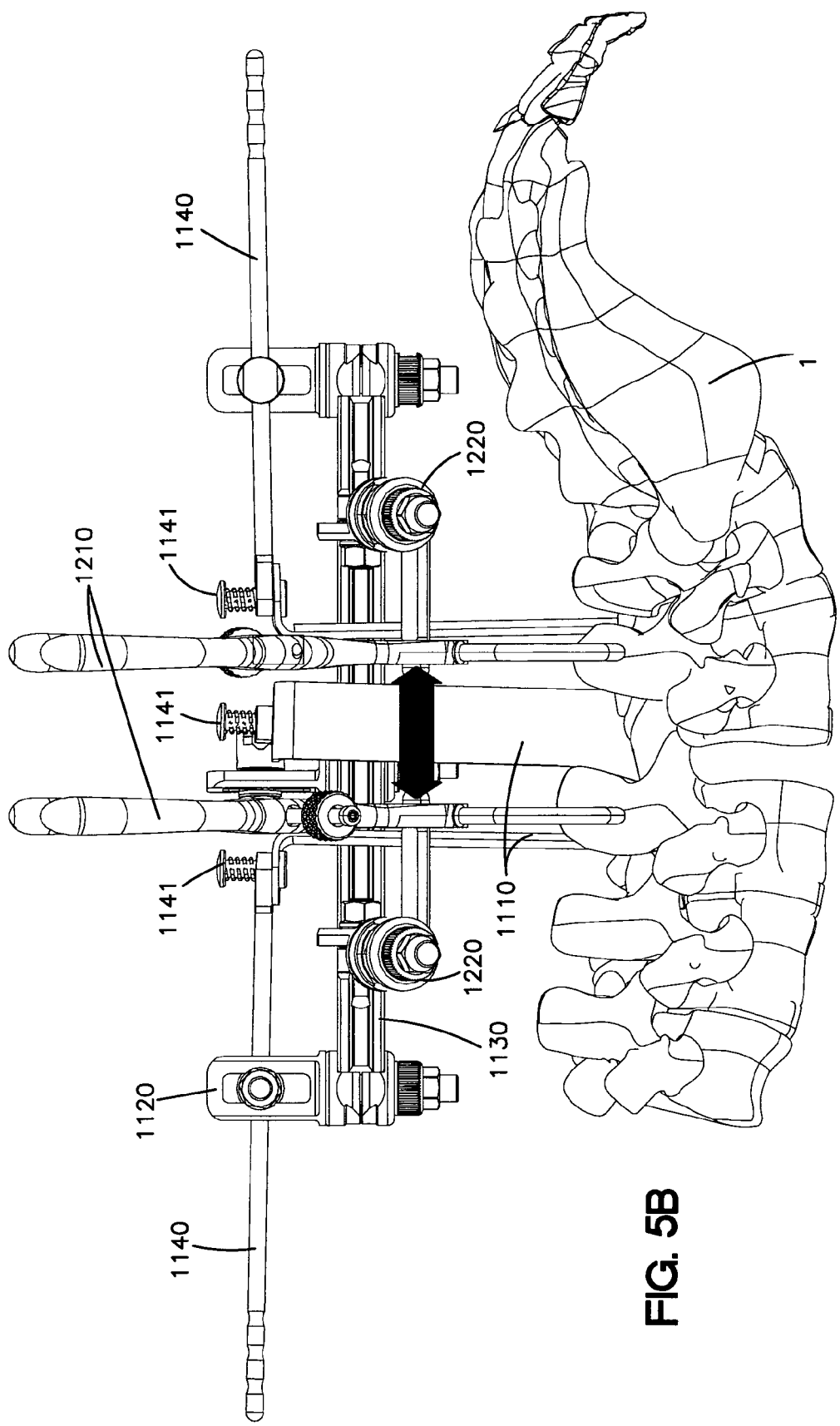

The spine retractor and distractor device 1000 also is able to perform distraction using the spinal processes 11, which are illustrated in FIG. 4. Distraction is possible because the retractor ring 1130 provides the necessary support to two or more spinal processes clamps 1210. With a distraction tool or pliers 1230, as shown in FIG. 11, an adequate distraction force can be applied to the spinal processes 11 as shown in FIG. 5A, or the spinal processes clamps 1210. The distraction movement, as shown in FIG. 5B, is a combination of translation and rotation of the vertebrae and consequently opens a foramen for implant insertion. The spine retractor and distractor device 1000 includes a distractor assembly 1200 which may comprise two or more spinal processes clamps 1210, preferably with locking mechanisms 1211 (see FIGS. 2A and 6A), and distraction pliers 1220 (see FIG. 11 for an example) configured to engage the spinal processes clamps 1210.

Figure 6B:
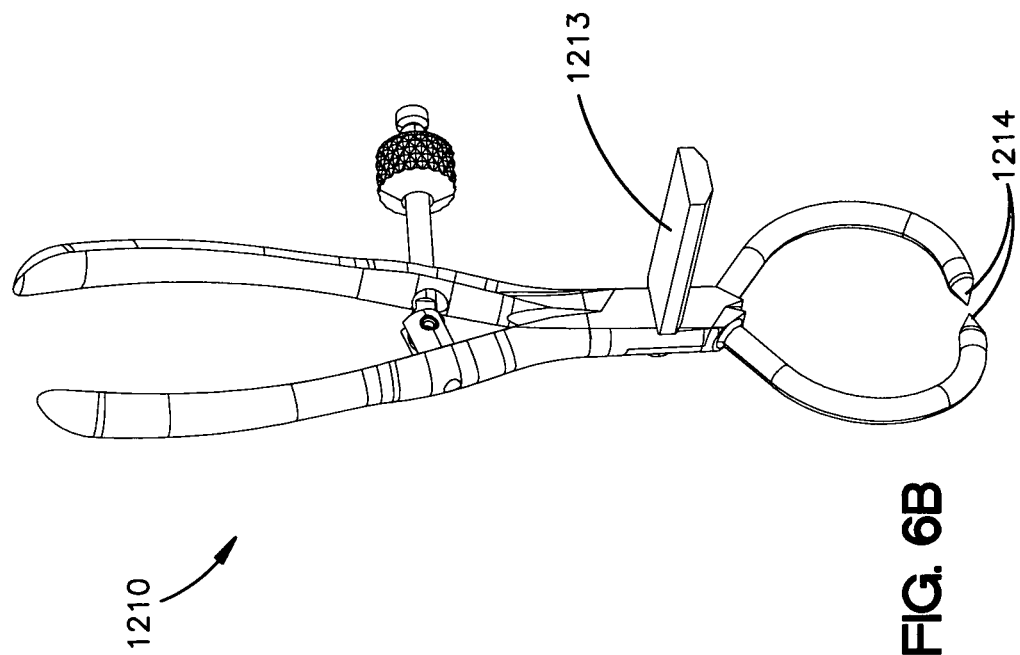
FIGS. 6A and 6b are perspective view illustrations of a spinal processes clamp according to an embodiment of the present invention.
Figure 6A:
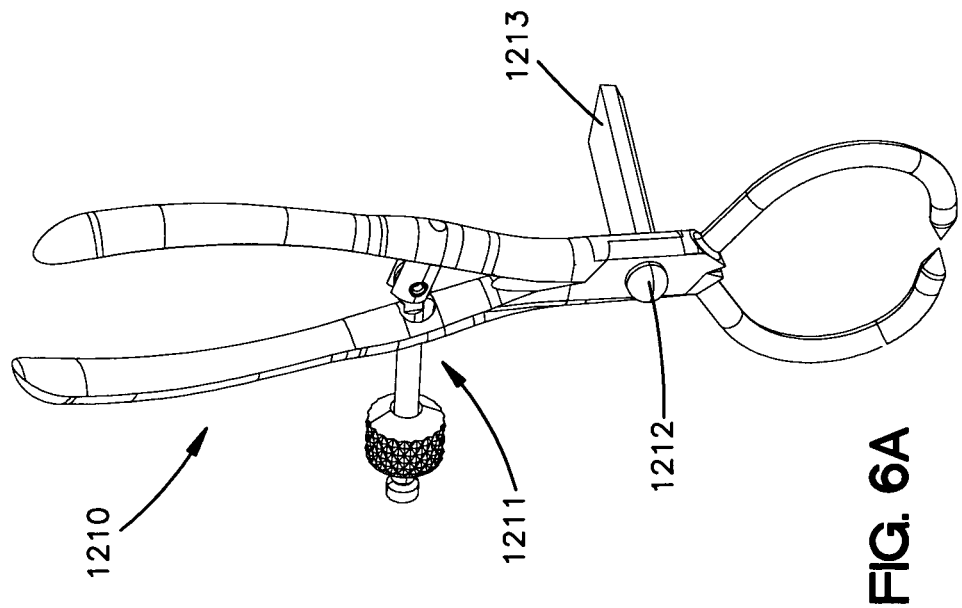

A spinal processes clamp or pliers 1210, for attaching onto the spinal processes 11, is shown in FIGS. 6A and 6B. The spinal processes clamp 1210 clamps to the spinal processes 11 and may provide for application of the distraction force to the spine. During use, the spinal processes clamps 1210 may grip the spinal processes 11 and can include a locking mechanism 1211. The spinal processes clamps 1210 allow for fixation of the retractor ring 1130.

So as to allow for translation, the spinal processes clamps 1210 have a translation guide 1213 (FIG. 6B) for guidance of the translation clamps 1220 which form a connection between the spinal processes clamps 1210 and the retractor ring 1130. The translation guide 1213 may be connected to the spinal processes clamp 1210 by a pin/distraction sphere 1212 which allows the translation guide 1213 to rotate about the pin 1212. The translation clamp 1220 may have an opening or guide 1222 which preferably is a dovetail guide, although other configurations are contemplated, for attaching onto the translation guide 1213 of the spinal processes clamp 1210. The translation clamp 1220 may move along the length of the translation guide 1213. As discussed previously, the retractor ring 1130 may have two ends that allow spinal process clamps 1210 to be attached. Each end 1131, 1132 of the retractor ring 1130 may have a set screw 1133 for attaching a translation clamp 1220 (FIG. 13) through an opening 1221 to the retractor ring 1130. The translation clamp 1220 may be secured to the retractor ring 1130 and set screw 1133 by a locking nut 1134. Although secured to the retractor ring 1130, the translation clamp 1220 has rotation means 1221 allowing rotation between the spinal processes clamps 1210 and the retractor ring 1130.

Distraction tool or pliers 1230, as shown in FIG. 11, may be used to apply a distraction force to the spinal processes 11, e.g., by way of the spinal processes clamps 1210. The distraction tool may be any tool or device capable of being disposed between two or more spinal processes 11, contacting or engaging the spinal processes clamps 1210, and applying an outward force to spread the spinal processes clamps 1210 apart. Because each spinal processes clamp 1210 is secured to a spinal processes 11, spreading the spinal processes clamps 1210 results in distraction of the spinal processes 11 and the corresponding vertebrae. In the embodiment shown in FIG. 11, suitable distraction pliers 1230 may include a pair of spreadable extensions 1235 operated, for example, by a handle 1233 and a hinge mechanism 1234. Each of the extensions 1235 may include an interface 1231, e.g., a depression, notch or other feature, configured to mate with a corresponding interface on a spinal processes clamp 1210, e.g., a distraction sphere 1212 as shown in FIG. 6A. A locking mechanism 1232 allows for a constant distraction force to be applied, without the surgeon maintaining a grip on the handle 1233 of the distraction pliers 1230.

A method of using the spine retractor and distractor device 1000 is depicted in FIGS. 2A and 2B. A surgeon mounts and locks two or more spinal processes clamps 1210 onto one or more spinal processes 11. The surgeon then attaches the retractor ring 1130 to the translation guide 1213 (as shown in FIG. 6B) on the spinal processes clamp 1210 by use of translation clamps 1220. In this manner, each end of the retractor ring 1130 is preferably attached to one of the spinal processes clamps 1210. The angle of the retractor ring 1130 may then be adjusted. The angle may be adjusted by rotating the translation guide about an axis extending through the translation guide. A support arm 1250 with an adjustable angle may also be used to assist with the adjustment of the angle of the retractor ring 1130. Retractor blades 1110 are attached with fixation clamps 1120 via rods 1140 and screws 1141 to the retractor ring 1130. The retractor blades 1130 and rods 1140 may be adjusted as necessary. The retractor blades 1110 are positioned to retract the soft tissue around the spinal processes 11 to expose a spine segment. This is accomplished by engaging the soft tissue with one or more retractor blades 1130. The surgeon may then distract the spinal segment using the distraction pliers 1230 engaged with one or more spinal processes clamps 1210.

In use, extensions 1235 of the distraction pliers 1230 may be disposed between the spinal processes clamps 1210 (as shown in FIGS. 7 and 8), and the distraction force can be applied by squeezing the handle portion 1233 of the distraction pliers 1230, which spreads the extension portion 1235. This corresponding distracts the spinal processes clamps 1210. Because the distraction force is a non-linear force, to maintain the reference with the patient, the translation clamp 1220 may correspondingly rotate via the rotating means 1221 as the spinal processes clamps 1210 are distracted. A locking mechanism 1232, as shown in FIG. 11, can be used to maintain the distraction force or position, e.g., by maintaining the handle 1233 of the distraction pliers 1230 in a particular state.

In one embodiment, the distraction pliers 1230 may be applied and used temporarily for the distraction movement. In other embodiments, the distraction pliers can be fixed to the spine retractor and distractor device 1000. One skilled in the art will appreciate that other distraction pliers, tools or mechanisms may be employed to impart a distraction force to one or more of the spinal processes clamps 1210 or one or more spinal segments.

The various components of the spine retractor and device 1000 may be made of alternative materials, for example PEEK or other materials in order to provide radiolucent properties for x-rays.

Although described with reference to the spinal processes 11, distraction can be attained over structures other than spinal processes 11. The system can also be utilized with pre assembled clamps or fixed clamps.

The spinal processes clamps 1210 may be designed with a single translation guide 1213, e.g., where just one clamp is fixed. The spinal processes clamps 1210 may have more than two points (tips) 1214. The spinal processes clamps 1210 and distractor pliers 1230 may have detachable handles.

The spine retractor and distractor device 1000 may be used without the retractor blades, but with a stand alone retractor. One or more additional guides for an implant holder may be used. Additional supports for the spinal processes clamps may or may not also be used.

Other embodiments of the spine retractor and device and methods described herein may be modified and used for other approaches in trauma or craniomaxillofacial (CMF) surgery. Other embodiments may be used in procedures involving the cervical spine.

While the foregoing description drawings represent preferred embodiments of the present invention, it will be understood that various additions, modifications and substitutions may be made therein without departing from the spirit and scope of the present invention. In particular, it will be clear to those skilled in the art that the invention may be embodied in or used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive.

What is claimed is:

1. An kit for retraction and distraction of a spine, comprising:
    at least two spinal processes clamps, each clamp configured to attach to spinal processes of a spine, each spinal process clamp rotatably connected directly to a translation guide and comprising an interface for mating with a corresponding interface on a distraction tool;
    a retractor ring having two ends and a translation clamp secured directly to each end and slidably coupled to one of the translation guides and, the retractor ring couplable to and angularly adjustable with the spinal processes clamps; and
    at least one retractor blade couplable to the retractor ring.

2. The kit according to claim 1, further comprising a distraction tool configured an interface for mating with the spinal processes clamp interface and, configured to provide a distraction force to the spinal processes.

3. The kit according to claim 2, wherein the distraction force provides translation and/or rotation of vertebrae.

4. The kit according to claim 1, further comprising a distraction tool configured to contact and apply a distraction force to the spinal processes.

5. The kit according to claim 1, further comprising one or more fixation clamps configured to rotatably couple the at least one retractor blade to the retractor ring.

6. The kit according to claim 5, further comprising a rod and a screw assembly for connecting the fixation clamps to the at least one retractor blade.

7. The kit according to claim 1, wherein the retractor ring has a fixed position with respect to the patient, and functions to retract soft tissue to provide access to a desired portion of the spine.

8. The kit according to claim 1, further comprising a light source and a camera.

9. The kit according to claim 1, wherein the retractor ring is in the shape of at least one of an oval and a polygon.

10. The kit according to claim 1, wherein the retractor ring is open.

11. The kit according to claim 1, wherein the retractor ring is C-shaped.

12. The kit according to claim 1, wherein the retractor ring is made of a material selected from at least one of the group of aluminum, stainless steel, PEEK (polyetheretherketone), and carbon fiber composite.

13. The kit according to claim 1, further comprising at least one support arm for maintaining a position reference on the patient.

14. The kit according to claim 1, wherein the at least one retractor blade is bendable.

15. The kit according to claim 1, wherein the spinal processes clamps further comprise a locking mechanism for locking the clamps with respect to the retractor ring.

16. A system for performing spinal retraction and distraction, the system comprising:
  at least two spinal processes clamps, each spinal processes clamp rotatably connected directly to a translation guide and comprising an interface for mating with a corresponding interface on a distraction tool, wherein each spinal processes clamp is secured to one or more spinal processes of a patient;
  a retractor ring having two ends and a translation clamp secured directly to each end and slidably coupled to one of the translation guides and thereby attached to the spinal processes clamps;
  at least one retractor blade coupled to the retractor ring and retracting soft tissue around the spinal processes to expose a spine segment; and
  a distraction tool comprising and interface coupled with the spinal processes clamp interface and applying a distracting force to the spinal segment.

17. The system according to claim 16, wherein the at least one spinal processes clamp comprises a pair of spreadable extensions.

18. The system according to claim 17, wherein the at least one spinal processes clamp comprises a pair of spreadable extensions operable by at least a handle and hinge mechanism.

* * * * *